US00PP16122P3

(12) United States Plant Patent
Palmer

(10) Patent No.: US PP16,122 P3
(45) Date of Patent: Nov. 15, 2005

(54) ***EUPATORIUM* PLANT NAMED 'LITTLE JOE'**

(50) Latin Name: *Eupatorium dubium*
Varietal Denomination: Little Joe

(75) Inventor: Angela Jo Palmer, Highland Park, IL (US)

(73) Assignee: CP Delaware, Inc., Wilmington, DE (US)

( * ) Notice: Subject to any disclaimer, the term of this patent is extended or adjusted under 35 U.S.C. 154(b) by 105 days.

(21) Appl. No.: 10/728,955

(22) Filed: Dec. 8, 2003

(65) Prior Publication Data

US 2005/0125869 P1 Jun. 9, 2005

(51) Int. Cl.[7] ..... A01H 5/00
(52) U.S. Cl. ..... Plt./263
(58) Field of Search ..... Plt./263, 226

(56) References Cited

PUBLICATIONS http://www.plantdelights.com/Catalog/Current/page31.html.*

* cited by examiner

*Primary Examiner*—Kent Bell
*Assistant Examiner*—W. C. Haas
(74) *Attorney, Agent, or Firm*—Burns, Doane, Swecker & Mathis, LLP

(57) ABSTRACT

A new and distinct variety of *Eupatorium dubium* plant is provided that was discovered while growing among a population of seedlings in a nursery at Jennersville, Pa. A stiffer more upright and more compact growth habit is displayed. The attractive light lavender inflorescence also is more compact. Superior drought tolerance has been observed. The new variety is particularly well suited for providing attractive ornamentation in smaller landscapes and for growing in areas that experience less rainfall.

4 Drawing Sheets

Botanical/commercial classification: *Eupatorium dubium*/*Eupatorium* Plant.

Varietal denomination: cv. 'Little Joe'.

SUMMARY OF THE INVENTION

The new *Eupatorium dubium* plant was discovered while growing among a population of seedlings of this species in a nursery setting at Jennersville, Pa., U.S.A. The exact parentage of the new variety is unknown. I was primarily initially attracted to a single plant of the new variety in view of its more compact upright growth habit and more compact inflorescence. The single plant of the new variety was carefully preserved and evaluated. Had this plant not been discovered and preserved it would have been lost to mankind.

It was found that the new *Eupatorium dubium* plant of the present invention exhibits the following combination of characteristics:

(a) forms a stiffer more upright and more compact growth habit, (b) displays an attractive more compact light lavender inflorescence, and (c) displays greater drought tolerance.

The new variety of the present invention can be readily distinguished from other plants of the species in view of the distinctive combination of characteristics described herein.

The new variety well meets the needs of the horticultural industry. It is particularly well suited for providing attractive ornamentation in smaller landscapes, and for growing in areas that experience diminished rainfall.

The new variety has been found to undergo asexual propagation at West Grove, Pa., U.S.A. by division and by the use of cuttings. Asexual reproduction by these routes in Pennsylvania has shown that the combination of characteristics is firmly fixed and is strictly transmitted to subsequent generations.

The new variety has been named 'Little Joe'.

BRIEF DESCRIPTION OF THE PHOTOGRAPHS

The accompanying photographs show as nearly true as it is reasonably possible to make the same in color illustrations of this character typical specimens of the plant and plant parts of the new variety. The plants of the new variety were three years of age and were photographed during August and September 2003 while growing in the ground at Jennersville, Pa. Dimensions in centimeters are included at the bottom of FIGS. 3 and 4.

DETAILED DESCRIPTION

Figure 1:
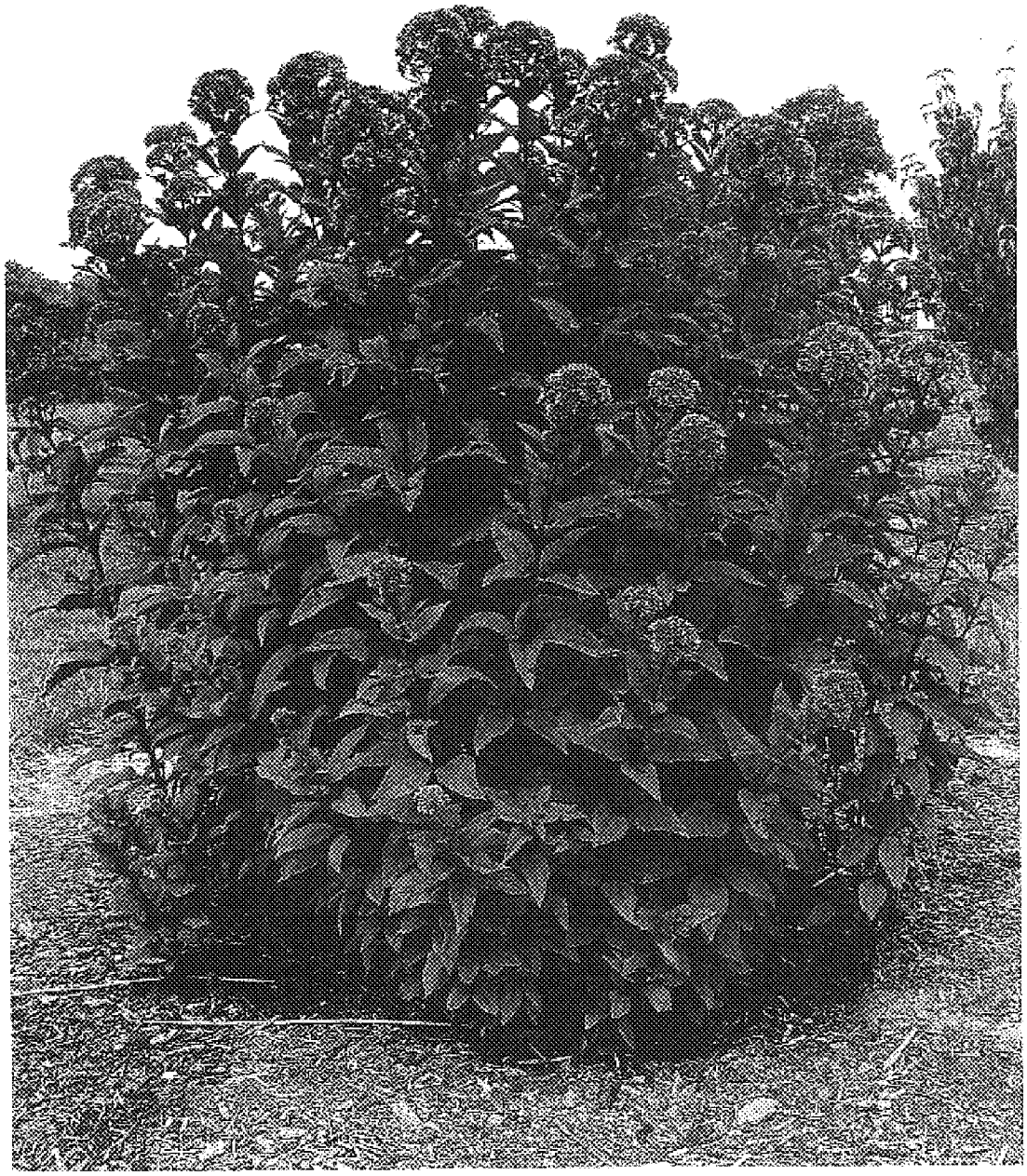
FIG. 1 illustrates an overall plant while blossoming in which the stiff upright and compact growth habit is displayed.

The chart used in the identification of colors is that of The Royal Horticultural Society (R.H.S. Colour Chart). General color terms are accorded their customary dictionary significance. The description is based upon the observation of a typical three-year-old plant of the new variety during August and September 2003 while growing in the ground at Jennersville, Pa., U.S.A.

Plant:

*Type.*—Herbaceous perennial.

*Height.*—Typically approximately 100 to 120 cm on average at the end of the growing season.

*Width.*—Typically approximately 90 to 100 cm on average at the end of the growing season.

*Growth habit.*—Stiff, upright and compact, and forms a relatively slow growing clump.

Stems:

*Color.*—Base coloration of mature stems commonly is near Green Group 143A and Yellow-Green Group 144B with spots of anthocyanin coloration near Purple Group 79B with some Purple Group 77A, 79A, and 79C, as well as Violet Group 83C.

Foliage:

*General appearance.*—Medium to dark green and semi-glossy.

*Arrangement.*—Verticillate, sometimes 3 and more typically 4 leaves at a node.

*Petioles.*—Typically approximately 4 to 11 mm in length, and approximately 1.3 to 1.8 mm in width measured at the base of the leaf blade.

*Leaves.*—Type: simple. Shape: typically lanceolate to occasionally narrowly ovate. Apex: narrowly acute. Base: narrowly cuneate. Texture: very rugose on the upper surface, similar to that of paper, and somewhat stiff. Size: varies somewhat with the season and water availability during growth. Commonly a mature leaf is approximately 5 to 13 cm (averages approximately 10 cm) in length, and approximately 2 to 6 cm (averages approximately 4.5 cm) in width. Venation: triple-veined with an elongate pair of basal lateral veins that is typical of the species. Color: near Green Group 137A on the upper surface, and near Green Group 137C on the under surface with midrib vein of near Green Group 138D.

Inflorescence:

*Type.*—A plurality of heads arranged in a corymb with perfect individual flowers.

*Buds.*—Color: prior to opening near Red-Purple Group 62B with some Red-Purple Group 62A, 65A, and 73C.

Figure 2:
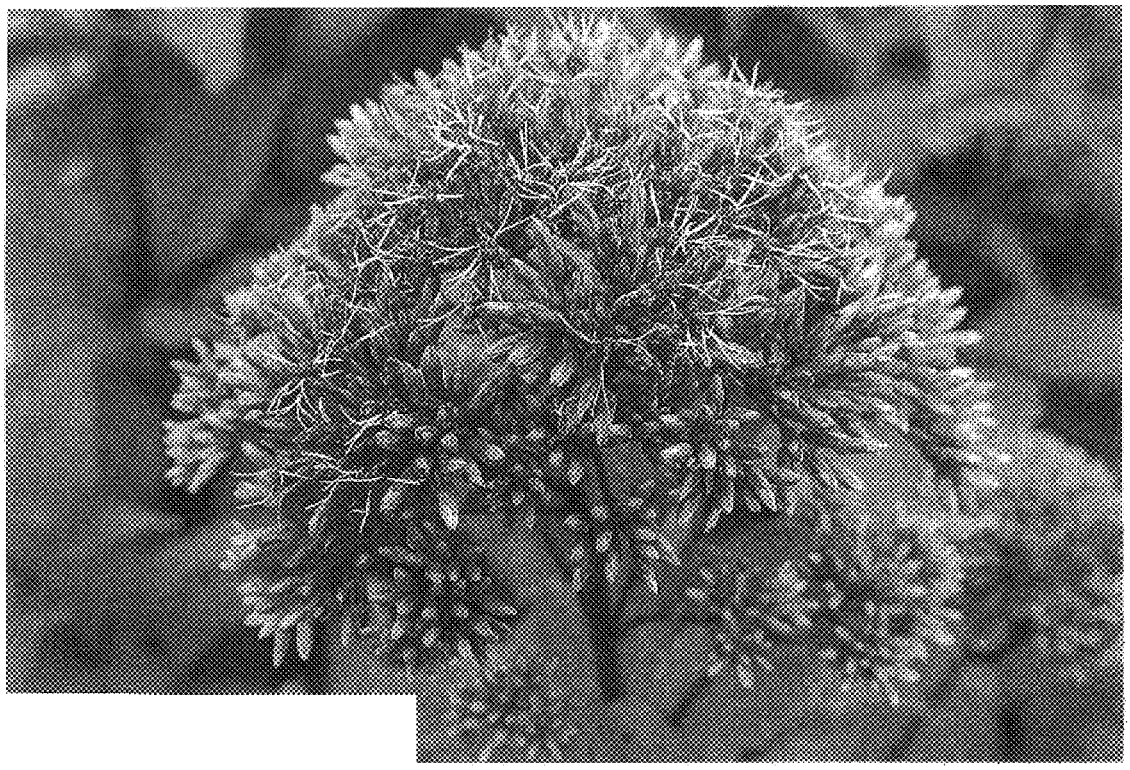
FIG. 2 illustrates a closer view of the generally compact inflorescence.
Figure 3:
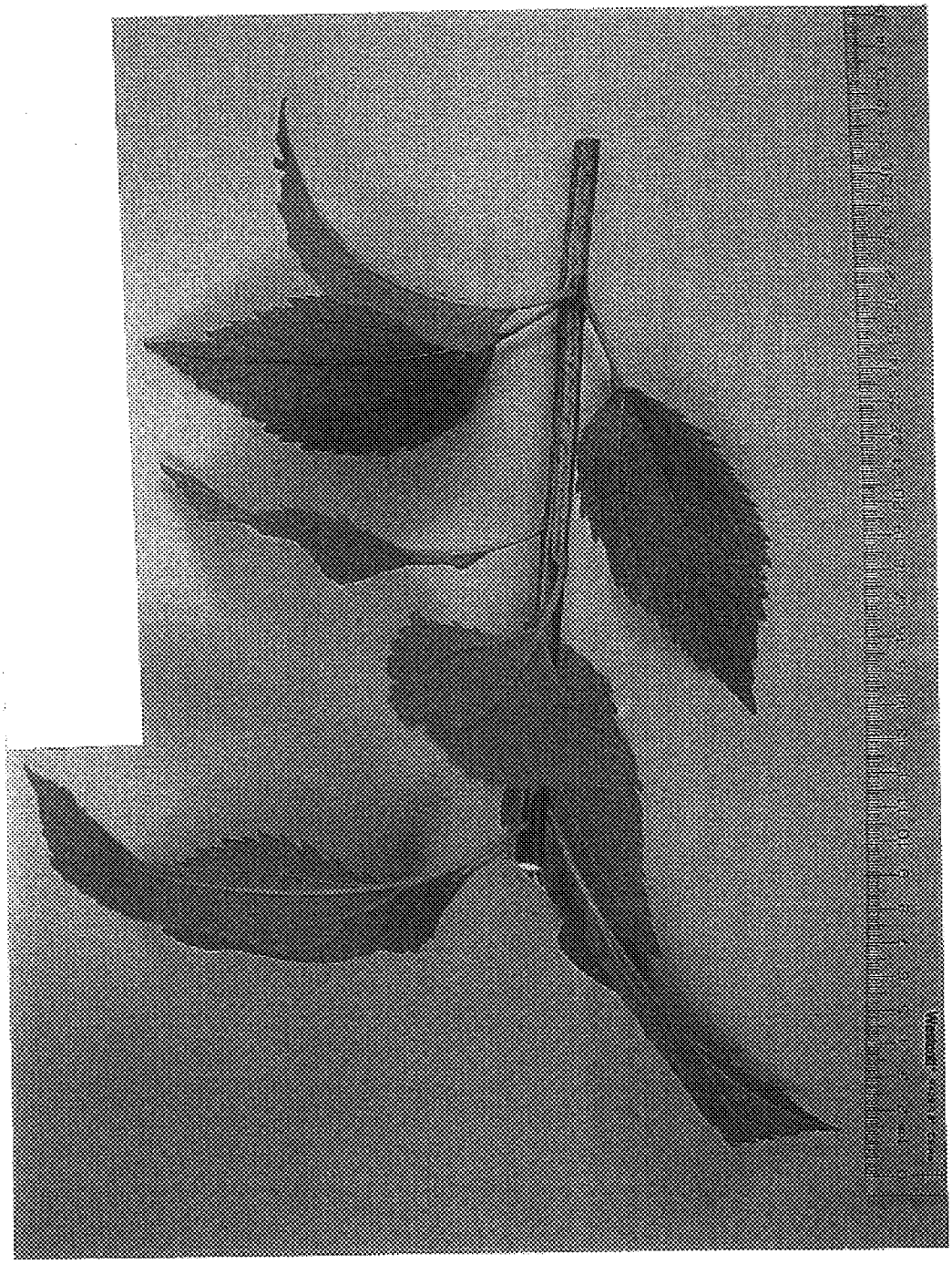
FIG. 3 illustrates a section of a typical stem while bearing leaves.
Figure 4:
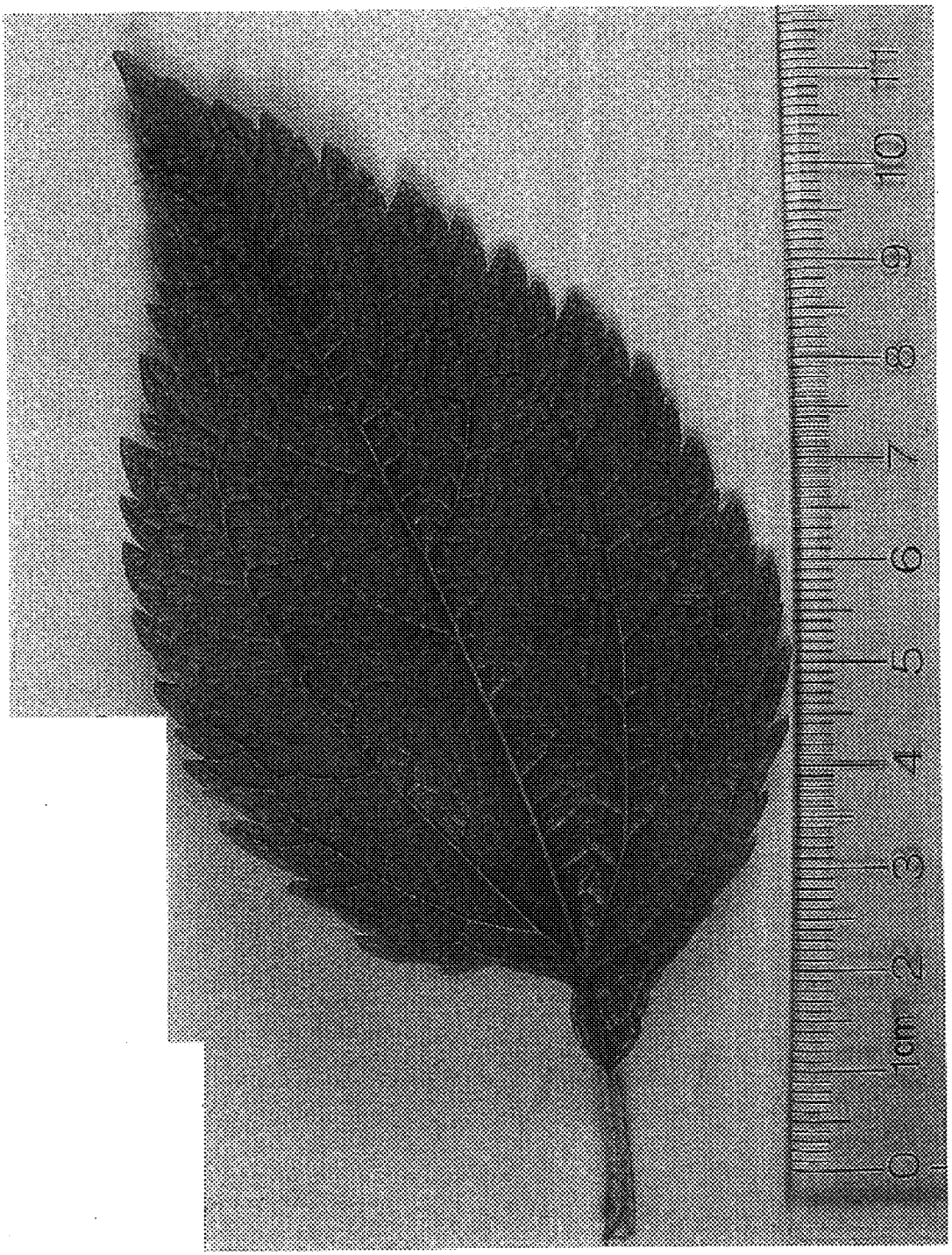
FIG. 4 illustrates an obverse view of a typical leaf.

*Flowers.*—Individual flowers commonly measure approximately 7 mm in length and approximately 2 mm in width, approximately 7 to 15 of these flowers commonly combine to form a flower head that commonly measures approximately 3 cm in length and approximately 2 cm in width, approximately 5 to 9 of the flower heads combine to form a compound inflorescence having a diameter of approximately 5 cm, and approximately 8 to 10 of the compound inflorescences combine to form an overall bloom having a diameter of approximately 13 cm as illustrated in FIG. 2. The coloration is near Red-Purple Group 69B commonly with some Red-Purple Group 71B at the apex, and much of the effective coloration is attributable to the visible nature of the extended styles and stigmas.

*Styles.*—One per floret, near Red-Purple Group 62C in coloration.

*Stigmas.*—One per floret, near Red-Purple Group 73C at the tip prior to the separation of the stigmatic tip, and thereafter near Red-Purple Group 62B.

*Stamen.*—Typically approximately 10 per flower.

Development:

*Blooming.*—Typically in August and continuing for approximately two to three weeks.

*Hardiness.*—Has withstood −20° F.

*Drought tolerance.*—Superior to that commonly displayed by the species.

*Disease resistance.*—Typical of species with no particular resistance or susceptibility to disease having been observed to date.

I claim:

1. A new and distinct *Eupatorium dubium* plant having the following combination of characteristics:

(a) forms a stiffer more upright and compact growth habit, (b) displays an attractive more compact light lavender inflorescence, and (c) displays greater drought tolerance;

substantially as illustrated and described.

* * * * *